United States Patent [19]

Layer et al.

[11] Patent Number: 5,378,229
[45] Date of Patent: Jan. 3, 1995

[54] CHECK VALVE MANIFOLD ASSEMBLY FOR USE IN ANGIOPLASTY

[75] Inventors: James Layer, Cooper City, Fla.; Andrea Slater, Somerville, N.J.

[73] Assignee: Cordis Corporation, Miami Lakes, Fla.

[21] Appl. No.: 186,666

[22] Filed: Jan. 25, 1994

[51] Int. Cl.$^6$ ............................................. A61M 5/00
[52] U.S. Cl. ...................................... 604/31; 137/512
[58] Field of Search .................. 604/30, 31, 247, 33, 604/35, 246, 249; 137/512

[56]  References Cited
U.S. PATENT DOCUMENTS

| | | | |
|---|---|---|---|
| 3,386,470 | 6/1968 | Goda et al. | 137/512 |
| 3,578,020 | 5/1971 | Rochte et al. | 137/512 |
| 4,447,230 | 5/1984 | Gula et al. | |
| 4,490,331 | 12/1984 | Steg, Jr. | |
| 4,858,619 | 8/1989 | Toth | 604/247 |
| 4,862,911 | 9/1989 | Yie | 137/512 |
| 5,020,562 | 6/1991 | Richmond et al. | 604/247 |
| 5,297,576 | 3/1994 | Weinheimer | 137/512 |

*Primary Examiner*—C. Fred Rosenbaum
*Assistant Examiner*—Manuel Mendez
*Attorney, Agent, or Firm*—Lockwood, Alex, Fitzgibbon & Cummings

[57] ABSTRACT

A check valve manifold assembly contains multiple inlet and outlet ports extending through a housing into a fluid passageway. The fluid passageway interconnects the various ports, and the housing further contains multiple check valves, one such valve being associated with each of the ports. When used with an active perfusion pump, the manifold system permits easy and proper perfusion of the patient at high pressures.

22 Claims, 3 Drawing Sheets

CHECK VALVE MANIFOLD ASSEMBLY FOR USE IN ANGIOPLASTY

BACKGROUND AND SUMMARY OF THE INVENTION

The present invention relates generally to equipment employed in the performance of angioplasty procedures including use within percutaneous transluminal coronary angioplasty (PTCA) systems and more particularly, to a check valve manifold assembly which interconnects a perfusion pump to a PTCA catheter or the like.

The use of inflatable balloon, or dilation, catheters in the treatment of coronary conditions is widespread. Catheters are used for a number of medical purposes, such as injecting radiopaque fluids into patient's body to perform an angiogram to locate blockage of arteries or other body vessels and expanding against such blockages to open them. Balloon catheters are used in expanding a blockage, commonly referred to as a stenosis, which is a narrowing or stricture of an artery or other body vessel.

In PTCA, a guide catheter is introduced into the artery of the patient and guided through the artery until the distal tip of the catheter is in the desired location of the coronary artery near the stenosis. A dilation catheter which has an inflatable balloon affixed to its distal end is then introduced along the guide catheter and advanced into the patient until the balloon end is located at the stenosis. Once located, the balloon is inflated so that it expands against the artery walls, thereby expanding, or dilating, the artery and compressing the stenosis This expansion often removes all of or a significant portion of the blockage. The balloon may be inflated against the arterial walls for only one specific time or it may be repeatedly inflated and deflated in a cycle matching the heartbeat of the patient.

Once the artery is expanded, the balloon is deflated and the balloon and guide catheters are removed so that blood may again flow through the artery. The literature describes a restenosis rate of about 15–30% which occurs in PTCA. Restenosis describes the situation where the arterial wall is expanded by the balloon and the arterial blockage is opened, but the arterial wall contracts and adopts its original, restricted state some time after the balloon is deflated and removed. There exists a belief that this restenosis rate can be lowered if longer inflation times are used during balloon catheterization procedures.

Longer balloon inflation times may be accompanied by a significant disadvantage: ischemia of the cardiac muscles. Ischemia is a local, or temporary, deficiency of oxygen in an area of the body caused by an obstruction in the blood vessel which supplies blood to that area. Because of the stenosis, the body parts or areas distal of the stenosis may already be in jeopardy.

In order to prevent ischemia, efforts have been made to develop coronary angioplasty catheters which are perfusion catheters; that is, they permit the flow of blood across or through the angioplasty balloon during inflation thereof. The perfusion of blood through a balloon catheter may be accomplished in several ways. The balloon may have one or more dedicated passages formed therein which define flow channels extending through the balloon from one end to the other and which permit the passage of blood through/across the balloon. A balloon catheter may also have a multi-lumen catheter in which one of the lumens serves exclusively as a passage to carry blood through the inflated balloon area.

Whatever the perfusion procedure and catheter structure, the blood preferably should be passed through the inflated balloon area at a specific flow rate to avoid ischemia, such as 60 cc per minute. This flow rate may be affected by certain variables, such as the diameter of the perfusion lumen which carries the blood. Because of the generally minute diameters of lumens used in PCTA procedures, an external or extracorporeal pump is commonly used to assist in the perfusion procedure, rather than rely upon the patient's heart to pump blood through the inflated balloon area. The extracorporeal pump receives blood from the patient and circulates it through the catheter and past the distal end of the balloon. These pumps may either be hand-operated syringes or conventionally powered pumps. Where syringes are used as the perfusion pumps, it is desirable to ensure continuous circulation of the blood, by the use of dual syringes connected such that as one syringe pumps blood into the patient through the balloon catheter, the other syringe draws blood from the patient into the pumping chamber and remains in a ready condition.

It is therefore desirable to provide a means for interconnecting perfusion pumps with a PCTA catheter and directing the flow of body fluids therefrom. It is especially desirable that such a means be compact and reliable and resistant to the high pumping pressures associated with perfusion.

Some extracorporeal manifolds exist, such as that described in U.S. Pat. No. 4,447,230 issued May 8, 1984. This manifold is used in association with intravenous administration of fluids and has a plurality of inlet ports arranged in an in-line fashion along a common axis in the form of tee-shaped members interconnected together. Each inlet port includes a check valve which permits one way flow of the fluids from a bag into the manifold, catheter and patient. In such an assembly, the ports and associated valves are designed for low pressures because they receive their fluids from solution bags in which the flow for intravenous administration is promoted by gravity rather than by an active pumping means.

Accordingly, it is an object of the present invention to provide an extracorporeal valve manifold assembly to use in PTCA procedures which manifold is resistant to high pumping pressures, is compact and permits interconnection of one or more perfusion pumps with a perfusion catheter and a supply catheter.

Another object of the present invention is to provide a check valve manifold assembly which is suitable for use in PCTA systems and which interconnects multiple perfusion pumps with a PCTA catheter and the patient.

Another object of the present invention is to provide a unique compact valve manifold assembly having a fluid passage which directs flow between an inlet and outlet, the assembly having a plurality of valves arranged in a housing, the fluid passage interconnecting the inlet and outlet with multiple pumping ports, each of the pumping ports having a check valve associated therewith capable of resisting high perfusion pumping pressures, in which the check valves are arranged so as to operate reliably regardless of whether blood is being perfused or aspirated.

The present invention accomplishes these objects by providing a compact valve manifold assembly having multiple valves in fluid communication with multiple ports of the manifold. These ports include a manifold inlet, a manifold outlet and one or more pump ports which are connected to multiple perfusion pumps. Two syringes may be used as perfusion pumps which are preferably synchronized so that when one of the two syringes is withdrawing, or aspirating, blood from a patient, the other syringe is pumping, or perfusing it back into the patient through the perfusion catheter to the distal end of the inflation balloon. The manifold includes a fluid passage in communicating with the inlet, outlet and pumping ports and having a plurality of check valves. The check valves may be located at equal distances within the fluid passage of the assembly so as to provide distinct flowpaths, or subpassageways with equal flow resistance so that no single flowpath has a pressure drop greater than the other. Additional ports may be provided in the assembly which communicate with the fluid passage to enable connection to the assembly of exterior fluid pressure actuated devices, such as pressure gauges and relief valves.

These and other objects, features and advantages of the present invention will be clearly understood through a consideration of the following detailed description.

BRIEF DESCRIPTION OF THE DRAWINGS

In the course of the following detailed description reference will be frequently made to the accompanying drawings in which.

DETAILED DESCRIPTION OF THE PREFERRED EMBODIMENTS

Figure 1:
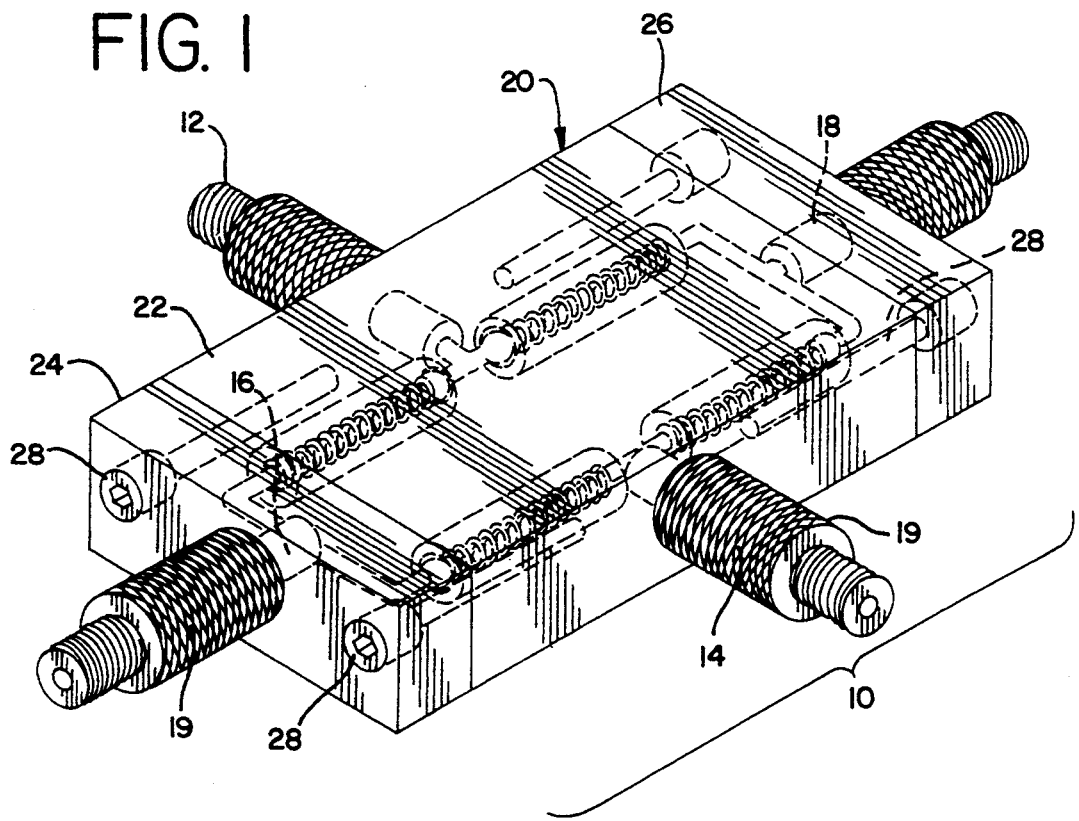
FIG. 1 is a perspective view of a check valve manifold assembly constructed in accordance with the principles of the present invention.
Figure 2:
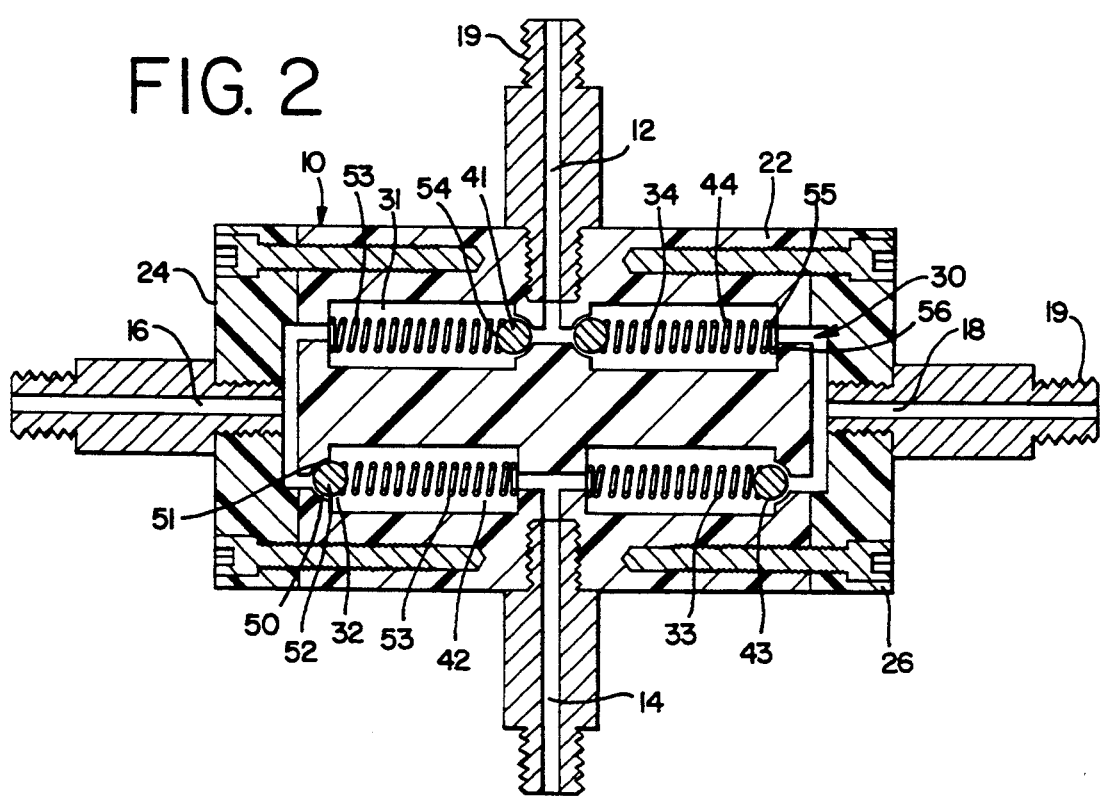
FIG. 2 is a sectional view of the check valve manifold assembly of FIG. 1.

Referring to the drawings, and particularly FIGS. 1 and 2, an extracorporeal valve manifold system generally designated at 10, for regulating the perfusion of blood during percutaneous transluminal coronary angioplasty (PTCA) is illustrated. The manifold assembly illustrated generally includes an inlet 12, an outlet and a plurality of pump ports 16, 18. The assembly 10 may have threaded connection members 19 attached thereto in communication with the ports 12, 14, 16 and 18 which provide a point of operative connection to equipment such as catheters, tubing, pumps and the like.

Figure 4:
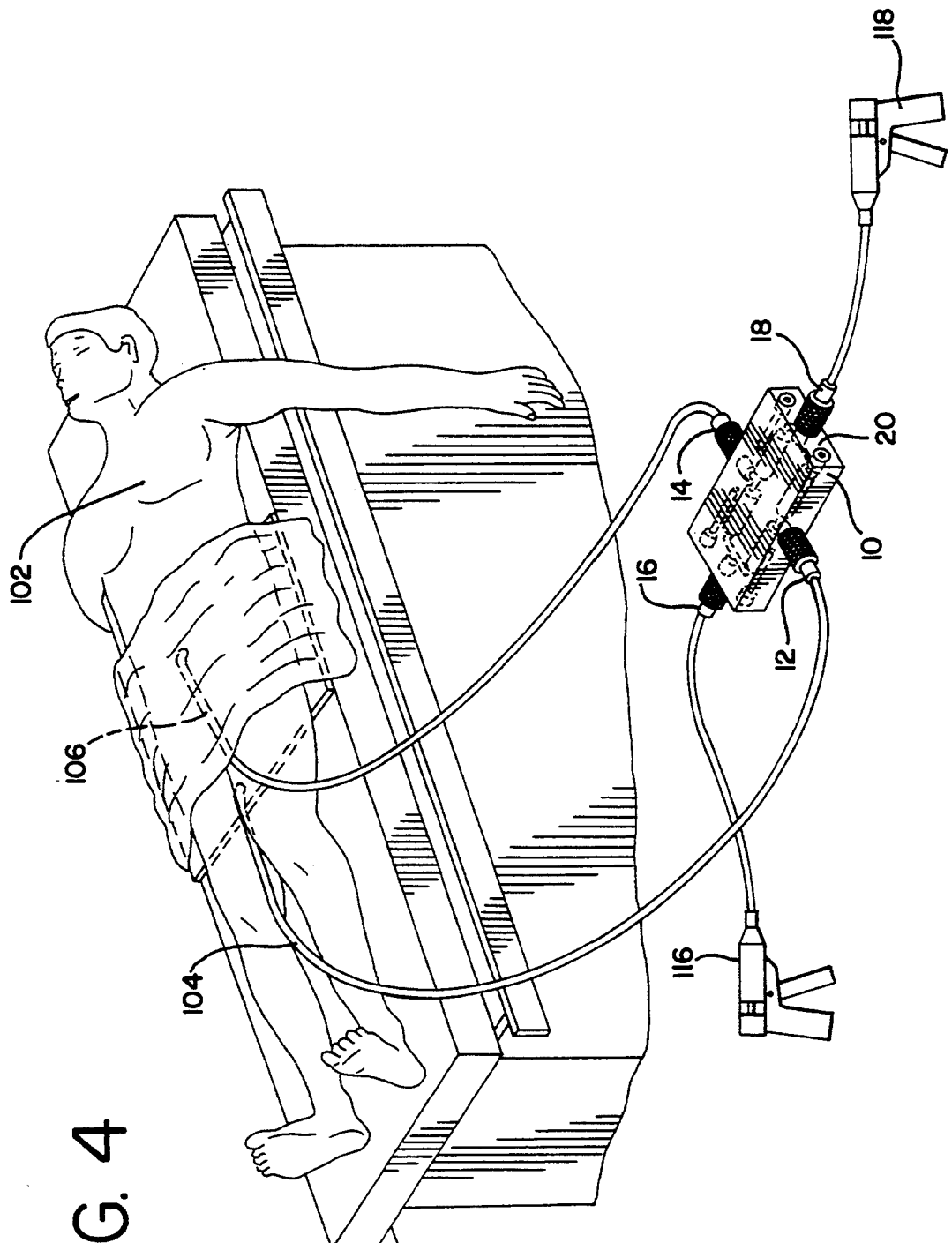
FIG. 4 is an overall view of a PTCA system using the manifold assembly of FIG. 1; and, FIG. 5 is a sectional view of another embodiment of a check valve manifold assembly constructed in accordance with the principles of the present invention.

The manifold assembly 10 of the present invention is particularly useful during PTCA procedures when a PTCA catheter is inserted into an artery of a patient 102 (FIG. 4) and guided to an area of an artery wherein a blockage, or stenosis occurs. The PTCA catheter includes an inflatable balloon (not shown) which is inflated when the balloon is located at the blockage site. During inflation, the balloon is expanded against the arterial walls and the blockage to exert pressure on the artery and blockage in order to widen the opening through the blockage. A lumen (also not shown) extends through the PTCA catheter and through the balloon and provides a passage for blood to be perfused into the patient to a location past the blockage so as to prevent deficiency of blood and oxygen in the areas distal of the balloon.

The patient's own blood is used in the PTCA procedure and is obtained from the patient 102 by means of an aspiration catheter 104 which is inserted in a conveniently located artery of the patient. Alternatively, the blood may be drawn from another source, such as a blood bag. When an aspiration catheter 104 is used, blood may be drawn through the catheter 104 by one or more perfusion pumps, $P_1$, $P_2$, illustrated in FIG. 4 as conventional syringe pumps 116, 118, respectively. The pumps may be synchronized such that as one syringe pump $P_1$ is operating in a suction stroke to draw blood from the patient 102 through an aspiration catheter 104, the other syringe pump $P_2$ is operating in a pumping stroke to pump blood previously drawn from the patient through the manifold assembly 10 and into the patient via PTCA catheter 106. The manifold assembly 10 interconnects the aspirating catheter 104, the perfusion catheter 106 and the two perfusion syringe pumps 116, 118.

Returning now to FIGS. 1 and 2, the internal construction of the manifold assembly 10 may best be understood as follows. In the embodiment illustrated, a manifold assembly 10 includes a manifold housing, or member 20, which may be integrally formed in one piece, or, as illustrated, may be formed from multiple components, such as a central portion 22 flanked by two opposing end portions 24 and 26. The end portions 24, 26 may be secured to the central portion 22 by a suitable means, such as screws 28. The valve manifold assembly 10 includes an internal fluid passageway 30 which is in the general nature of a loop as shown which interconnects the manifold inlet 12 and outlet 14 with the perfusion pumping ports 16, 18. As discussed herein, this loop is subdivided by suitable valving into two distinct flowpaths. The fluid passageway 30 may be either polygonal, such as rectangular, in cross-section, or it may be generally circular in cross-section as illustrated. The fluid passageway loop may be arranged in a rectangular loop as illustrated or may take other suitable configurations, such as a circular loop.

Four distinct valve chambers 31, 32, 33, 34 are defined in the housing 20 at spaced-apart locations along the fluid passageway 30. The chambers 31–34 are preferably located within the manifold housing 20 and fluid passageway 30 such that each valve chamber 31–34 is located between adjoining ports of the manifold assembly 10. For example, valve chamber 31 is disposed in the fluid passageway 30 between inlet 12 and pumping port 16, while valve chamber 32 is disposed between pumping port 16 and its adjoining port, outlet 14. Each valve chamber 31–34 has an individual valve assembly 41, 42, 43, 44 respectively, associated with it and disposed therein.

Each illustrated valve assembly 41–44 includes an arcuate valve seat 50 formed at one end of the valve chamber. The valve seat 50 preferably has an interior surface 51 which provides an efficient seal when it is engaged by a suitable check valve member. Such a surface may be frusto-conical or semispherical (as illustrated) and engages the ball or check valve member 52 shown. The ball check member 52 is preferably located in the chamber and is urged against the valve seat 50 by means of a helical coil spring 53. One end 54 of the coil spring bears against the ball check member 52 while its opposing end 55 bears against a shoulder 56 formed in the opposite end of the valve chamber.

Each of the valve assemblies 41–44 act as an individual check valve, meaning that each such assembly flow in only one direction in the fluid passageway 30. This flow is from behind the valve element 52 forwardly of and around the valve element 52 through the coil spring 53. The valve elements 52 are preferably highly polished for ease of movement and may be formed of any suitable and biocompatible materials which are non-reactive with body fluids and which may be easily sterilized, such as synthetic sapphire, synthetic ruby, stainless steel, elastomers, polycarbonates and teflon.

As check valves, the valve assemblies 41–44 define the distinct flowpaths, or fluid subpassageways $F_1$, $F_2$, within fluid passageway 30 each subpassageway $F_1$, $F_2$, extending between the inlet 12 and the outlet 14 of the manifold assembly 10. These flowpaths $F_1$, $F_2$ may be of equal length so that the resistance which fluids encounter in each flowpath is equal and thus no flowpath creates a greater pressure drop than the other. Although ball check valves are illustrated, it will be understood that other valve elements which are operative in response to fluid pressure will fall within the scope of the present invention, such as a cylindrical, stepped plug elemenmt which engages a cylindrical annular surface of the valve chamber with a compliant member associated therewith.

Basically, the valve manifold assembly 10 normally operates in conjunction with one or more perfusion pumps 116, 118 (FIGS. 3A-B & 4) and maintains the flow of blood from one perfusion pump $P_1$ while the other perfusion pump $P_2$ is aspirating, or removing, blood from the patient 102. The perfusion pumps $P_1$, $P_2$ may take the form of hand operated syringe pumps as shown (FIG. 4) or they may take the form of any other suitable pumping means. They may be individually operated or interconnected such that one is aspirating blood while the other is perfusing it. The operation of this system is shown in FIGS. 3A and 3B which illustrate the flow of blood through the manifold assembly 10 during pumping and suction strokes of the two perfusion pumps $P_1$ and $P_2$ interconnected to the ports 16 and 18 respectively.

Figure 3A:
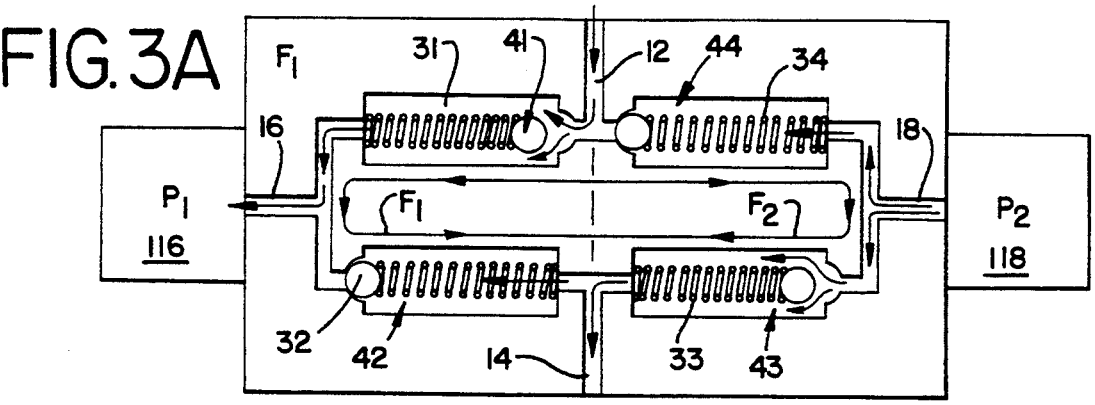
FIG. 3A is a schematic view of the check valve manifold assembly of FIG. 1 showing its manner of operation under a first flow condition.
Figure 3B:
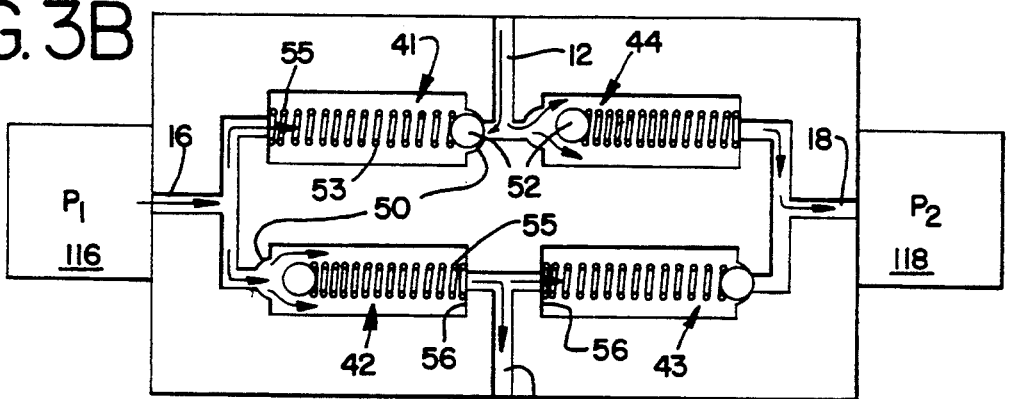
FIG. 3B is a schematic view of the check valve manifold assembly of FIG. 1 showing its manner of operation under a second flow condition.

FIGS. 3A and 3B schematically illustrate the operation of the manifold assembly 10 during a PTCA procedure and best illustrate how the valve assemblies 41–44 separate the fluid passageway 30 into two separate flowpaths $F_1$ and $F_2$ in response to the pumps $P_1$ and $P_2$. In these Figures, the arrows illustrate the flow of blood into, through and out of the manifold assembly 10. For example, in FIG. 3A blood enters the inlet 12 while one perfusion pump $P_1$ (116) is in a suction mode, i.e., withdrawing blood from the patient, while the other perfusion pump $P_2$ (118) is simultaneously pumping or expelling blood previously gathered from the patient through port 18 into the manifold assembly 10 and out through the outlet 14 thereof.

In this sequence, the suction created by pump $P_1$ simultaneously opens valve assembly 41 and closes the valve assembly 42, thus defining the flowpath $F_1$ and permitting fluid flow on this flowpath from inlet 12 to port 16. In the illustrated embodiment, the valve element of valve assembly 41 is urged against its associated coil spring, thereby permitting flow of blood through the valve chamber 41 (as shown by the arrows). At the same time, pump $P_1$ applies a suction force against the valve element of valve assembly 42 to close that valve and prevent flow of blood toward perfusion pump $P_1$ from either perfusion pump $P_2$ or the manifold outlet 14. This suction force is assisted by positive fluid pressure from pump $P_2$.

Perfusion pump $P_2$, which is in its positive pumping stroke also shown in FIG. 3A, expels blood through the port 18 into the flowpath $F_2$ and against the valve elements of valve assemblies 44 and 42 proximate to the inlet 12 to close it and prevent flow of blood from pump $P_2$ out of the manifold assembly 10 through the inlet 12. The flow of blood from $P_2$ opens the valve element of valve assembly 43, and blood passes through the valve 43 and out of the manifold assembly 10 via the outlet 14. During this flow of blood, the blood impinges against the valve element of valve assembly 42 to ensure that it is sealed and blood will not enter the other flowpath $F_1$ leading to perfusion pump $P_1$.

FIG. 3B illustrates the relative positions of the check valves of the manifold assembly 10 after blood has been completely expelled from perfusion pump $P_2$ and pump $P_1$ has been filled with blood by the action shown in FIG. 3A. The entire assembly operates in a manner opposite to that shown in FIG. 3A. For example, blood pumped from pump $P_1$ enters the remaining portion of flowpath $F_1$ and seals valve assembly 41 while opening valve assembly 42 by which blood can only flow from pump $P_1$ out through the manifold outlet 14. This outflow of blood also seals valve 41 to prevent blood expelled from pump $P_1$ from entering pump $P_2$ or exiting the manifold assembly 10 through the inlet 12. Simultaneously, when pump $P_2$ is on its suction stroke, valve assemblies 41 and 43 are further urged to close due to the suction head applied within that passageway by pump $P_2$, while valve assembly 44 opens to create the first half of flowpath $F_2$ which permits the flow of blood through the inlet 12 into pump $P_2$ and eventually out of the outlet 14.

Figure 5:
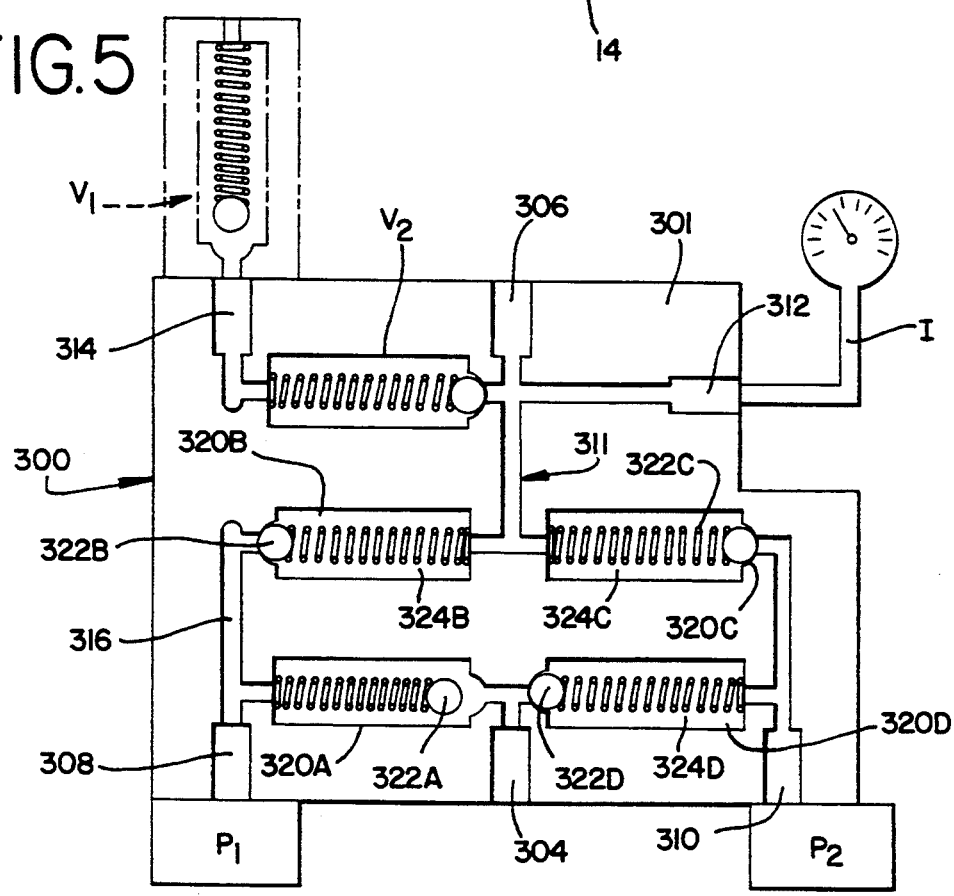

FIG. 5 illustrates another embodiment of a check valve manifold assembly 300 constructed in accordance with the principles of the present invention. The manifold assembly 300 includes ports which permit the attachment of external, pressure actuated components to the manifold assembly 300.

As depicted in FIG. 5, the assembly housing 302 includes a number of openings, such as fluid inlet 304, fluid outlet 306, first pumping port 308, second pumping port 310, a first additional port 312 adapted to receive a connection from a pressure indicating means, such as pressure gauge I and a second additional port 314 adapted to receive a connection from a pressure relief valve V.

The housing 301 of the manifold assembly 300 has a modified fluid passageway 311 which leads to the various openings described above. As shown, an additional opening 312 is located in the housing 302 proximate to the fluid outlet 304 and between same and the loop portion 316 of the passageway 311. The opening preferably receives a connection from a pressure indicating means, such as the pressure gauge I (shown schematically) to enable the operator to monitor the pressure of the fluid(s) being transmitted through the assembly 300. The housing 301 may also include a second additional opening 314 located proximate to the fluid outlet 306 and between same and the fluid passageway loop portion 316, which is adapted to receive a connection to an external pressure relief valve V (shown in phantom) or an internal pressure relief valve $V_2$ which prevents overpressurization of the supply catheter.

With the exception of the two additional openings 312 and 314, the structure of the assembly 300 is generally the same as that of the first embodiment described above. The assembly 300 contains multiple valve chambers 320 positioned along the fluid passageway 311, which chambers further contain valve elements 322A-D and valve springs 324A-D, such that when the assembly 300 is interconnected to the pumps $P_1$, $P_2$, the valve elements 322A-D react in accordance to their orientation within the assembly housing 301.

The manifold assembly 10 of the present invention lends itself to being easily manufactured by economical methods such as injection molding. It has been determined through testing that the manifold assembly of the present invention easily accommodated the high pumping pressure required to maintain a flow rate of 60 cc/min to a patient. This testing has determined that the manifold assembly may withstand pumping pressures of approximately 300 psi up to approximately 500 psi. These high pumping pressures are dictated by the relatively small cross-sectional size of the perfusion catheter, which may approach 0.018 inch.

While the preferred embodiments of the invention have been shown and described, it will be understood by those skilled in the art that changes or modifications may be made thereto without departing from the true spirit and scope of the invention.

We claim:

1. An extracorporeal valve manifold assembly for use in association with a perfusion pump in percutaneous transluminal angioplasty procedures, the manifold assembly comprising:
    a housing, a fluid passageway defined within the housing; a plurality of openings disposed in said housing, each of the openings communicating with the fluid passageway and said fluid passageway extending within said housing in a loop to interconnect all of said openings together, one of said openings constituting an inlet to said manifold assembly and another, opposite one of said openings constituting an outlet from said manifold assembly; said manifold assembly further containing a plurality of discrete valve assemblies, said valve assemblies being disposed in said housing along said fluid passageway such that each said valve assembly is disposed generally between adjoining openings of said housing; each of said valve assemblies forming an individual check valve to define a plurality of discrete fluid pathways, whereby flow of fluid directed into said manifold assembly via said inlet is directed through said fluid passageway to a fluid receiving component, and flow of fluid from a fluid providing component to the manifold assembly is directed through said fluid passageway and out of said manifold assembly via said outlet.

2. The manifold assembly of claim 1, wherein said housing includes four valve assemblies, each one positioned between two of said inlets, an opening to the fluid receiver, said outlet end and opening to the fluid provider.

3. The manifold assembly of claim 2, wherein one pair of said four valve assemblies are disposed in said housing proximate to said inlet and a second pair of said four valve are disposed in said housing proximate to said outlet, whereby said first pair of valve assemblies directs fluid flow in said fluid passageway away from said inlet and to the fluid receiving component while preventing fluid flow from said inlet to the fluid providing component, and whereby said second pair of valve assemblies directs fluid flow in said fluid passageway from said fluid providing component to said outlet while preventing fluid flow from said fluid providing component to said inlet, and said first and second pairs of valve assemblies automatically change fluid flow paths when said fluid receiving component becomes a said fluid providing component and said fluid providing component becomes said fluid receiving component.

4. The manifold assembly of claim 1, wherein each of said valve assemblies includes a spherical valve element, semispherical valve seat and means for urging said valve element towards said valve seat.

5. The manifold assembly of claim 1, wherein said fluid passageway has a substantially circular cross-section.

6. The manifold assembly of claim 1, wherein said housing is a multi-component member having a central portion and two opposing end portions which, when assembled together cooperate to define said fluid passageway.

7. The manifold assembly of claim 1, wherein said housing is made from a biocompatible material.

8. The manifold assembly of claim 7, wherein said biocompatible material is a transparent polycarbonate.

9. The manifold assembly of claim 1, wherein said housing includes at least one additional opening proximate to said manifold assembly outlet which additional opening provides an interconnection between said fluid passageway and an exterior pressure-actuated component.

10. Manifold apparatus for channeling flow of body fluids, such as blood, from an inlet to an outlet of said manifold apparatus while passing the fluid through at least one pumping means of multiple pumping means associated with the apparatus, said manifold apparatus comprising a housing having an inlet, an outlet and two ports disposed in said housing between said inlet and outlet thereof, each of said ports being adapted for fluid communication with one of said multiple pumping means, said housing further having an interior fluid chamber defining a fluid flowpath, the fluid chamber having a plurality of valve assemblies disposed therein such that one valve assembly is located along said fluid flowpath between adjoining ones of said housing inlet, outlet and ports, said valve assemblies each defining a check valve, said check valves operating in response to a pressure differential within said manifold apparatus created by said multiple pumping means to separate said fluid flowpath into two, separate fluid subflowpaths in fluid communication between said housing inlet and outlet, each of said fluid subflowpaths being in fluid communication with at least one of said ports and one of said multiple pumping means associated therewith.

11. Apparatus according to claim 10, wherein each of said check valves includes a valve seat, a valve member which engages said valves seat to seal said check valve and biasing means for biasing said valve member towards said valve seat.

12. Apparatus of claim 10, wherein said fluid flowpath has a generally circular cross-section and each of said fluid subflowpaths are of substantially the same length from said inlet to said outlet.

13. A check valve manifold assembly for use in an active perfusion pumping system having at least two perfusion pumps, the manifold assembly comprising an inlet, an outlet and at least two interconnecting ports which allow for the passage of body fluids in and out of said manifold assembly to and from the perfusion pumps, the inlet being adapted to receive a connection from a blood supply source, the outlet being adapted to receive a connection from a treatment catheter inserted into the patient, the manifold assembly having a fluid passageway which interconnects said inlet, said outlet and two pumping ports together in fluid communication, said manifold assembly further including a plurality of check valves disposed at predetermined locations along said fluid passageway said check valves being located in said fluid passageway between adjoining ones of said inlet, outlet and pumping ports, said check valves cooperating to define distinct fluid flowpaths of equal extent extending between said inlet and said outlet, each of said fluid flowpaths intersecting and communicating with one of said two pumping ports to thereby permit body fluid flow into said manifold assembly via said inlet and out of said manifold member via said outlet, while preventing body fluid flow out of said manifold assembly via said inlet.

14. The valve manifold assembly of claim 13, wherein said check valves cooperate such that said distinct fluid flowpaths change to accommodate reversal of flow of said two perfusion pumps between pumping and aspirating modes of each said perfusion pump.

15. The valve manifold assembly of claim 13, wherein each of said check valves includes a valve seat, a ball valve member which engages said valve seat to seal said check valve, and biasing means for urging said ball member towards said valve seat.

16. The valve manifold assembly of claim 13, wherein said two fluid flowpaths are defined by a passageway housing a substantially circular cross-section.

17. The valve manifold assembly of claim 13, wherein said manifold assembly has a housing molded from a biocompatible material.

18. The manifold assembly of claim 13, further including a first additional port which is adapted to receive a connection from a fluid pressure indicating means.

19. The manifold assembly of claim 18, further including a second additional port which is adapted to receive a connection from a fluid pressure relief valve.

20. An extracorporeal valve manifold assembly for use in association with a perfusion pump in percutaneous transluminal angioplasty procedures, the manifold assembly comprising:

a housing, a fluid passageway of a substantially circular cross-section defined within the housing, a plurality of openings disposed in said housing, each of the openings communicating with the fluid passageway such that said fluid passageway interconnects all of said housing openings together, one of said openings constituting an inlet to said manifold assembly and another one of said openings constituting an outlet from said manifold assembly; said manifold assembly further containing a plurality of discrete valve assemblies, said valve assemblies being disposed in said housing along said fluid passageway such that each said valve assembly is disposed generally between adjoining openings of said housing; each of said valve assemblies forming an individual check valve to define a plurality of discrete fluid pathways, whereby flow of fluid directed into said manifold assembly via said inlet is directed through said fluid passageway to a fluid receiving component, and whereby flow of fluid from a fluid providing component to said manifold assembly is directed through said fluid passageway and out of said manifold assembly via said outlet.

21. A check valve manifold assembly for use in an active perfusion pumping system having at least two perfusion pumps, the manifold assembly comprising an inlet, an outlet and at least two interconnecting ports which allow for the passage of body fluids in and out of said manifold assembly to and from the perfusion pumps, the inlet being adapted to receive a connection from a blood supply source, the outlet being adapted to receive a connection from a treatment catheter inserted into the patient, the manifold assembly having a fluid passageway which interconnects said inlet, said outlet and two pumping ports together in fluid communication, said manifold assembly further including a plurality of check valves disposed at predetermined locations along said fluid passageway, one of said check valves being located in said fluid passageway between adjoining ones of said inlet, outlet and pumping ports, said check valves cooperating to define distinct fluid flowpaths extending between said inlet and said outlet, each of said fluid flowpaths intersecting and communicating with one of said two pumping ports to thereby permit body fluid flow into said manifold assembly via said inlet and out of said manifold member via said outlet, while preventing body fluid flow out of said manifold assembly via said inlet, said manifold assembly further including an additional port which provides an interconnection between said fluid passageway and an exterior pressure actuated component.

22. A check valve assembly for a body fluid pumping system having at least two perfusion pumps, comprising: a housing having an inlet, an outlet and two interconnecting ports which allow for the passage of body fluids in and out of said housing to and from the perfusion pumps; a fluid passageway disposed within said housing; a series of check valves disposed in communication with the fluid passageway, said check valves cooperating to define distinct fluid flowpaths extending between said inlet and said outlet, whereby each of said fluid flowpaths communicate with a different interconnecting port to thereby permit body fluid flow into said housing via said inlet and out of said housing via said outlet while preventing body fluid flow out of said housing via said inlet.

* * * * *